(12) United States Patent
Schoemaker et al.

(10) Patent No.: US 6,444,207 B1
(45) Date of Patent: Sep. 3, 2002

(54) IMMUNOTHERAPY OF TUMOR WITH MONOCLONAL ANTIBODY AGAINST THE 17-1A ANTIGEN

(75) Inventors: Hubert J. P. Schoemaker, Devon; Richard A. Carrano, Phoenixville, both of PA (US)

(73) Assignee: Centocor, Inc., Malvern, PA (US)

( * ) Notice: Subject to any disclaimer, the term of this patent is extended or adjusted under 35 U.S.C. 154(b) by 0 days.

(21) Appl. No.: 08/307,044

(22) Filed: Sep. 16, 1994

Related U.S. Application Data

(63) Continuation of application No. 07/726,640, filed on Jul. 2, 1991, now abandoned, which is a continuation of application No. 07/384,073, filed on Jul. 20, 1989, now abandoned, which is a continuation of application No. 06/883,572, filed on Jul. 9, 1986, now abandoned.

(51) Int. Cl.$^7$ ............................................. A61K 39/395
(52) U.S. Cl. ................................ 424/156.1; 530/388.85
(58) Field of Search .......................... 424/155.1, 174.1, 424/277.1, 156.1, 141.1; 530/388.8, 388.1, 387.1, 828, 388.85; 435/240.27

(56) References Cited

U.S. PATENT DOCUMENTS 4,579,827 A * 4/1986 Sakamoto et al.
4,925,922 A * 5/1990 Byles et al.

FOREIGN PATENT DOCUMENTS

EP 0199141 * 10/1986 ................. 435/240

OTHER PUBLICATIONS

Kahzaeli et al, *Proc. AACR* 27:331 1986 (abst.).*
Lagliahue et al, *Hybridoma* 5(2) 1986, p. 107–115.*
Schyoff et al, *Cancer Res* 45, 1985, p. 879–85.*
Harris et al, *TIBTECH* vol. 11, Feb. 1993, pp. 42–44.*
Molecular Foundation of Oncology, ed Broder, 1991, pp. 9–134.*
Sears, *Cancer Res* 45, 1985, p. 5910–13.*
Lindholm et al, *Int Archs Allergy Appl. Immun.* 71, 1983 p. 178–81.*
Gottlinger et al, *Hybridoma* 5, 1986, p. 529–37.*
Sun, et al, *Hybridoma* 5, 1986 p. 517–20.*
Steplewski *Hybridoma* 5, 1986 (pages vary) 51–185.*
Goettlinger et al. *Int. J Cancer* 38, 1986, p. 47–53 (abst.).*
Khazaeli et al. Proc. Am. Assoc. Cancer Res Annu Meeting 27, 1986, p. 331.*
Herlyn et al, *J. Immunol Methods* 85(1) 1985, p. 27–38.*
Sears, H.F. et al., J. Biol. Response Modifiers, 3:138–150, 1984.*
Sindelar, William F. et al., Hybridoma, 5(Suppl 1):5125–5132, Apr. 2, 1986.*
Khazaeli, M. et al., Proceedings of AACR, 27:331, Mar. 1986.*
Sears, H.F. et al., Can. Research, 45:5910–5913, Nov. 1985.*
Gottlinger, H.G. et al, Int. J. Cancer, 38:47–53, 1986.*
Schlimok, G. et al., Hybridoma, 5(Suppl 1):S163–S170, Apr. 2, 1986.*
Frödin, J.E. et al., "Treatment of Patients with Metastasizing Colo–Rectal Carcinoma with Mouse Monoclonal Antibodies (Moab 17–1A): A Progress Report", *Hybridoma*, 5(1):S151–S161 (1986).
Lobuglio, A.F. et al., "Phase I Clinical Trial of CO17–1A Monoclonal Antibody", *Hybridoma*, 5(1): S117–S123 (1986).
Herlyn, M. et al., "CO17–1A and Related Monoclonal Antibodies: Their Production and Characterization", *Hybridoma*, 5(1):S3–S10 (1986).
Ross, A.H. et al., "Isolation and Characterization of a Carcinoma–Associated Antigen", *Biochem. and Biophy. Research Communications*, 136(1):297–303 (1986).
Göttlinger, H.G. et al., "The Epithelial Cell Surface Antigen 17–1A, A Target for Antibody–Mediated Tumor Therapy: Its Biochemical Nature, Tissue Distribution and Recognition by Different Monoclonal Antibodies", *Intl J. of Cancer*, 38(1):47–53 (1986).
Mellstedt, H. et al., "Repeated High Doses of MAB 17–1A in the Treatment of Metastazising Colo–Rectal Carcinomas", *Hybridoma*, 6(2):Abstract (1987), presented at the 6th Annual Hybridoma Congress, Mar. 1–4, 1987, San Francisco, CA.
Khazaeli, M. et al., "Pharmacokinetics and Immune Response of Repeated Large Doses of Mouse Monoclonal Antibody 17–1A", *Clinical Research*, 35(1):44A (1987).
Herlyn, D.M. et al., *Cancer Res.* 40:717–721 (1980).
Herlyn, D. and Koprowski, H., *Proc. Natl. Acad. Sci. USA* 79:4761–4765 (1982).
Schroff, R.W. et al., *Cancer Res.* 45:879–885 (1985).

* cited by examiner

*Primary Examiner*—Sheela Huff
*Assistant Examiner*—Larry R. Helms
(74) *Attorney, Agent, or Firm*—Hamilton, Brook, Smith & Reynolds, P.C.

(57) ABSTRACT

Disclosed is a method for treating a gastrointestinal tumor by administering a murine antibody which specifically binds an epitope of 17-1A antigen.

17 Claims, No Drawings

IMMUNOTHERAPY OF TUMOR WITH MONOCLONAL ANTIBODY AGAINST THE 17-1A ANTIGEN

RELATED APPLICATION

This application is a continuation of U.S. Ser. No. 07/726,640, filed Jul. 2, 1991, now abandoned, which is a continuation of U.S. Ser. No. 07/384,073, filed Jul. 20, 1989, now abandoned, which is a continuation of U.S. Ser. No. 06/883,572, filed Jul. 9, 1986, now abandoned.

BACKGROUND

The tumoricidal activity of the murine monoclonal antibody 17-1A has been characterized in the nude mouse and in humans. See, e.g., Herlyn, D. and Koprowski, H. (1982) "IgG2a Monoclonal Antibodies Inhibit Human Tumor Growth Through Interaction with Effector Cells" *Proc. Natl Acad. Sci.* USA 79, 4761–4765. Several cases have been reported where the administration of Mab 17-1A resulted in a partial or complete regression of metastatic colorectal or pancreatic carinomas. See Sears, H. F. et al. (1984) "Effects of monoclonal antibody immunotherapy on patients with gastrointestinal adenocarcinoma." *J. Biol. Resp. Mod.* 3, 138–150; Sears, H. F., et al., "Phase II Clinical Trial of a Murine Monoclonal Antibody Cytotixic for Gastrointestinal Adenocarcinoma" (1985) *Cancer Res.* 45: 5910–5913. Generally, the antibody has been administered as single administration of 500 µg or less.

SUMMARY OF THE INVENTION

This invention pertains to a method of immunotherapy of gastrointestinal tumors employing multiple, high doses of murine monoclonal antibody against the gastrointestinal tumor-associated antigen 17-1A. The method comprises administering to a patient afflicted with gastrointestinal tumor, murine monoclonal antibody against the antigen 17-1A in multiple, sequential doses of about 100 mg or more for a total overall dose of from about 0.1 to about 5 grams. Each dose of the murine antibody can be administered at one to three day intervals up to weekly intervals to achieve and maintain a "continuous" high level of circulating antibody. Mixtures ("cocktails") of two or more murine anti-17-1A antibodies can be given. The multiple, high dose therapy can be performed as adjuvant therapy to chemotherapy, radiotherapy or surgery.

The high dose murine antibody therapy is well tolerated in patients. Further, the anti-murine antibody response which generally develops in treated humans, surprisingly does not alter significantly the plasma half life of the murine antibody on repeat administration. Thus, high blood levels of antibody can be achieved with sequential injections of high doses to enhance transit of the antibody from intravascular space into the tumor bed and thus provide higher concentrations of the therapeutic antibody to the locus of action.

DETAILED DESCRIPTION OF THE INVENTION

This invention pertains to therapy of gastrointestinal tumors with repeated, high dose of murine antibody against the 17-1A antigen associated with most gastrointestinal tumors. This therapeutic approach is based upon several findings. Murine anti-17-1A antibody administered in multiple, high dose is generally well-tolerated by patients. The most common side effect is mild gastrointestinal symptoms. Allergic responses, however, do limit repeat therapy in some patients. In addition, although a human anti-murine antibody response is generally evoked by the murine antibody, the response does not drastically effect the pharmacokinetics of the administered murine antibody. This indicates that sequential, high doses of antibody can be given to achieve and maintain a continuous high plasma level of antibody. Maintaining a high circulating level of antibody optimizes transit of the antibody from intravascular space into the tumor, thereby enhancing access of the antibody to the tumor for more effective anti-tumor action. Further, sustained, high blood levels lead to a prolonged, higher concentration of antibody at the locus of action for more effective antibody dependent cell mediated cytolysis of the tumor cells.

According to the method of this invention, murine antibody against the 17-1A antigen is administered to patients afflicted with gastointestinal tumors in multiple doses of about 100 mg or more, preferably about 400 mg –1 gram, for a total dose of about 0.1 to 5 grams, preferably 1 to 5 grams. The antibody is administered parenterally preferably by intraveneous infusion. The antibody is generally administered suspended in a physiologically acceptable vehicle e.g. normal saline. The antibody doses can be given over intervals of 1–3 days to intervals of about a week. The dose regimen for an individual patient will depend, inter alia, on the patient's clinical status and on his ability to tolerate the dose without detrimental allergic or anaphylactic reaction. The objective is to provide antibody at fractional doses which yields a sustained, high plasma level of antibody over the course of therapy to provide increased access of the antibody to the tumor site.

Murine antibodies against 17-1A can be administered individually or in mixtures (cocktails) of two or more murine anti-17-1A antibodies. Preferably, anti-17-1A antibody having different epitopic specificity for 17-1A is employed in the combination in order to increase anti-tumor activity in an additive or synergistic fashion. Murine antibodies can be selected from the original 17-1A antibody or other murine antibodies which recognize similar or different epitopes of the 17-1A antigen, such as the M72, M74, M77 and M79 antibodies described below.

Murine antibody against 17-1A antigen can be used in passive immunotherapy of tumors of the gastrointestinal tract with which the 17-1A antigen is associated. Examples are gastrointestinal adenocarcinoma, colorectal carcinoma and pancreatic carcinoma. The murine antibody treatment can be adjuvant to other forms of therapy, including chemotherapy, radiotherapy and/or surgery. In particular, murine antibody therapy can be useful as adjuvant therapy directed against micro- or mini-metastases which are not amenable to surgical removal.

The invention is further illustrated by the following exemplification.

Exemplification

A trial was conducted in 20 patients to examine patient tolerance to repeated high doses in 17-1A, to examine its pharmacokinetics on repeated administration and to characterize the human immune response (antibody) to this mouse immunoglobulin.

Patient Population

Twenty patients with gastrointestinal malignancy (17 colon; 2 gastric; and 1 pancreatic) were selected on the basis that they had metastatic disease with small-moderate tumor burden; performance status greater than 70% (Karnofsky scale) and objectively measurable disease. Studies were not done to document 17-1A reactivity with individual patient tumor specimens. Seven out of 20 patients had received prior chemotherapy while 13/20 had no prior therapy for metastatic disease.

Treatment Protocol

The study was conducted the Clinical Research Unit, Comprehensive Cancer Center, University of Alabama at Burmingham. All antibody infusions utilized a total dose of 400 mg of 17-1A diluted in 250 ml of normal saline infused over 30 minutes with careful monitoring of vital signs. All infusions were preceded by an intravenous test dose of 0.7 mg followed by 30 minutes of monitoring prior to administration of the full dose infusion. The protocol involved the accrual of 4 groups of 5 patients each who would receive progressively increasing numbers of weekly infusions, i.e. Group 1—5 patients—single infusion; Group 2—5 patients with 2 infusions—Day 1 and 8; Group 3—5 patients with 3 infusions—Day 1, 8 & 15; Group 4— 5 patients with 4 infusions—Day 1, 8, 15 & 22. Because of toxicity noted in Group 3 patients, no patients received 4 infusions, but these 5 patients were added to Group 2 and had 2 infusions of therapy (Day 1 & 8). All patients were followed for 6 weeks, following their last infusion with weekly monitoring of urinalysis, liver and renal function, blood counts and clinical evaluation.

Pharmacokinetics

Pharmacokinetic analysis was done on the first 5 patients at the time of their single infusion (no prior exposure to 17-1A), the ten patients who had two infusions were studied at the time of their second infusion (one prior exposure to 17-1A) and the group 3 patients were studied at the time of their third infusion (two prior exposures to 17-1A). For pharmacokinetics, blood samples were drawn prior to infusion, immediately at conclusion of infusion and at ½, 1, 2, 4, 12, 24, 48, 72 hours and 86 hours. Spot samples were drawn at pre-therapy, 1, 24 & 48 hours post-therapy on infusions not undergoing a full pharmacokinetic study to confirm the general pattern of mouse immunoglobulin disappearance. The plasma level of 17-1A was quantitated using a solid phase radiometric sandwich assay utilizing latex beads coated with rabbit anti-mouse gammaglobulin and radiolabeled ($^{125}$I) affinity purified goat antimouse IgG, F(ab')$_2$. The concentration of 17-1A in plasma was quantitated by the amount of latex particle binding of radiolabeled anti-mouse IgG, F(ab')$_2$ as compared to a standard curve of known concentrations of 17-1A diluted in normal plasma. The sensitivity of this assay was 1.0 ng/ml.

Human Anti-mouse Antibody (HAMA) Response

Serum samples were drawn on each patient prior to each infusion and then weekly×6. The assay used to determine the presence of human anti-17-1A was a "double antigen" system (Addison, G. and Hale, C., Horm. Metab. Res. 3, 59–60 (1971)) using the concurrent incubation of 17-1A coated latex beads, 100 ul of test plasma of 1 ug of radiolabeled ($^{125}$I) 17-1A (specific activity of 300–400 cpm/ng). The samples were incubated 90 minutes at room temperature and the radioactivity associated with the beads determined by centrifugation of the beads through Percoll as previously described (Lobuglio, A. et al., New Engl. J. Med. 309, 459–463 (1983)). The cpm of $^{125}$I-17-1A bound to the beads by plasma was converted to ng of 17-1A/ml of plasma by using the known specific activity of $^{125}$I-17-1A. This assay obviously detects any molecule with more than one binding site for 17-1A (IgG and IgM). Assay results in normal individuals and cancer patients prior to 17-1A exposure were 5±4 ng/ml plasma (n=54) with values ranging from 0 to 16 ng/ml. Values greater than 20 ng/ml were classified as an antibody response.

17-1A Monoclonal Antibody

The monoclonal antibody was provided by Centocor, Inc. as a purified suspension of 10 mg/ml in normal saline. It was stored at 4° C. prior to use. The protocol was carried out under Centocor sponsored IND (#2168).

Toxicity

The adverse effects of 17-1A administration are summarized in Table 1.

TABLE 1

TOXICITY ASSOCIATED WITH 17-1A INFUSION

| | |
|---|---|
| I. | Single dose (400 mg) - 5 patients |
| | 3/5 - none |
| | 2/5 - G.I. symptoms |
| II. | Two weekly doses (400 mg) - 10 patients |
| | 4/10 - none |
| | 5/10 - G.I. symptoms |
| | 1/10 - flushing/tachycardia |
| III. | Three weekly doses (400 mg) - 5 patients |
| | 3/5 - none |
| | 2/5 - G.I. symptoms and anaphylaxis |
| | (third dose) |

Ten of 20 patients had no adverse effects including 4 patients who received two infusions and 3 patients who received three infusions. The most frequently observed side effect was gastrointestinal (9/20 patients) with nausea and vomiting (4 patients) or diarrhea with or without cramps (7 patients). The symptoms usually began within an hour of infusion and lasted less than 24 hours. They were of modest-moderate severity and readily controlled with anti-emetics of anti-diarrhea medications. The frequency of gastrointestinal symptoms was not related to the number of 17-1A infusions. One patient had an episode of flushing and tachycardia in the midst of her second infusion which disappeared by simply slowing the infusion rate. This patient had no other adverse effects with the infusion nor with her prior infusion.

Two patients had serious adverse effects. Both patients had nausea and vomiting associated with their first and second infusions (Day 1 & 8). They tolerated their test dose of 17-1A on Day 15 without adverse effects over 30 minutes of observation. The treatment infusions were then begun and both developed dyspnea, tachycardia and hypotension judged to be an anaphylactic reaction. Both infusions were immediately stopped (less than 10% of dose given) and patients responded well to therapy with corti-costeroids, epinephrine and antihistamines. No patient in the study developed abnormalities of urinalysis, complete blood count, renal or hepatic function.

Pharmacokinetics

The serial plasma 17-1A levels on each patient were analyzed and found to fit will with a 1 compartment model of plasma disappearance. The results for peak plasma concentration, plasma half-life and area under the curve are summarized in Table 2.

TABLE 2

PHARMACOKINETICS 17-1A (400 mg) IN MAN

| Prior Antibody | Peak Conc. (ug/ml) | Half-life (hours) | AUC (hrs-ug/ml) |
|---|---|---|---|
| None (n = 5) | 139 ± 8 | 15 ± 2 | 3013 ± 175 |
| One (n = 10) | 141 ± 5 | 14 ± 1 | 2828 ± 93 |
| Two (n = 3) | 108 ± 2 | 24 ± 2 | 3771 ± 81 |

Values are expressed as mean ± standard error of the mean.
AUC = area under the curve.

The two patients who had anaphylactic reactions did not receive their full third dose of 17-1A and therefore had no pharmacokinetic study. Thus, only 3 patients made up the group with two prior exposures to 17-1A. The results are similar for all 3 groups of patients. The three patients studied on their third infusion had a somewhat lower serum peak concentration of 17-1A and a somewhat longer mean plasma half-life than the groups of patients with a single or second infusion. Interpretation is limited since the differences were modest and the group was made up of a small number of patients.

Human Anti-mouse Antibody (HAMA) Response

The patients' serum prior to therapy had little or no detectable ability to bind $^{125}$I-17-1A coated beads. As summarized in Table 3, almost all patients developed HAMA within 29 days of their first 17-1A exposure (17/20). The majority (11/20) had HAMA by Day 8 with 8/11 having values of greater than 100 ng/ml and 2/11 having values of greater than 1000 ng/ml. Peak values were generally noted on Day 15 or 22 with values falling by day 29 and beyond. Patients who received one, two or three exposures to 17-1A had similar degrees by HAMA response as summarized in Table 4.

TABLE 3

HUMAN ANTI-MOUSE ANTIBODY (HAMA) RESPONSE*

| | |
|---|---|
| Pre-therapy | 0/20 had antibody (range - 0–15 ng/ml) |
| Day 8 | 11/20 had antibody (range - 36–106 ng/ml) |
| Day 15 | 15/20 had antibody (range - 27–5598 ng/ml) |
| Day 22 | 14/20 had antibody (range - 60–5046 ng/ml) |
| Day 29 | 15/20 had antibody (range - 23–4900 ng/ml) |
| No antibody | 3/20 |

*Antibody activity expressed as ng of $^{125}$I-17-1A bound/ml Plasma.

TABLE 4

DEGREE OF HUMAN ANTI-MOUSE ANTIBODY (HAMA) RESPONSE*

| Exposures | Very High (>1000) | | Moderate (40–999) | | Poor/none (<40) | |
|---|---|---|---|---|---|---|
| Single | 3 | (60%) | 1 | (20%) | 1 | (20%) |
| Double | 4 | (40%) | 4 | (40%) | 2 | (20%) |
| Triple | 2 | (40%) | 2 | (40%) | 1 | (20%) |

*Expressed as ng of 17-1A bound/ml plasma

The two patients with anaphylactic reactions were interesting. They has HAMA levels of 1055 and 264 ng/ml on Day 8 and 1716 and 3745 ng/ml on Day 15, respectively. They tolerated their infusions of antibody on Day 8 without adverse effect except for nausea and vomiting (similar to what they had on Day 1 infusion) but had anaphylactic reactions on Day 15 at the time of their third infusion. A total of 11 infusions were administered to patients when their HAMA levels were greater than 20 ng/ml (elevated) with five having no side effects, three gastrointestinal symptoms, one flushing/tachycardia and two anaphylactic reactions. No patients developed fever, proteinuria or renal impairment.

It was also interesting that in nine of these 11 infusions, adequate plasma samples were available to determine peak plasma concentration and plasma half-life of 17-1A antibody. These values were not substantially different than infusions in the absence of detectable HAMA.

Discussion

This phase I/II study of repeated administration of 400 mg 17-1A monoclonal antibody provides several observations. In general, the administration of antibody was well tolerated in patients receiving one or two infusions. The mild gastrointestinal symptoms were clearly related to antibody infusion and were not a serious clinical problem. The pathogenesis of these symptoms is not known but does not seem related to an allergic reaction since they occurred just as frequently during a patient's first infusion as compared to third infusion. They may be related to the ability of this antibody to bind to normal gastrointestinal mucosa (Sears, H., et al., Surg. Res. 31, 145–150 (1981)). Two of five patients receiving three weekly infusions of 17-1A had anaphylactic reactions. This frequency of a potentially lifethreatening allergic reaction precluded our testing a four-dose schedule (weekly) and would deter treatment schedules requiring antibody administration on Day 15.

The pharmacokinetic studies indicate that this dose of antibody can achieve plasma concentrations of 100–200 ug/ml with a plasma disappearance curve approximating observations with other mouse monoclonal antibodies (radiolabeled) administered at much lower doses (Pimm, M., et al., J. Nucl. Med. 26, 1011–1023 (1985) and Rosenblum, M., et al., Cancer Res. 45, 2382–2386 (1985)). This plasma half-life results in plasma concentrations of less than 1 ug/ml by day 8. Thus, maintenance of a substantial plasma concentration of 17-1A would require administration more frequently than weekly. Prior studies (Pimm, M., et al., J. Nucl. Med. 26, 1011–1023 (1985) and Larson, S., et al., J. Nucl. Med. 24:123-129 (1983)) have suggested that the appearance of HAMA response is associated with a dramatic alteration in circulating levels of mouse Ig. Our failure to observe this phenomenon is somewhat surprising. However, it should be noted that our antibody measurements are expressed in terms of ng 17-1A bound/ml plasma with an infusion of 17-1A which readily achieves concentrations of 100–200 ug/ml in the circulation. We are currently modifying our HAMA assay to allow quantitation of total circulating HAMA. This may clarify whether the patient's total circulating HAMA is able to bind only a small fraction of this large circulating dose of 17-1A.

We did not find evidence of pre-existing human anti-mouse antibody (17-1A) prior to antibody infusion as reported by others (Schroff, R., et al., Cancer Res. 45, 879–885 (1985)). We initially attempted to assay for human anti-mouse antibody using an assay which detected human immunoglobulin binding to 17-1A coated beads using radio-labeled monoclonal mouse anti-human Fc antibody. We found that normal individuals and cancer patients prior to monoclonal antibody infusion had varying quantities of human immunoglobulin which bound non-specifically to 17-1A coated beads. This binding did not have classic competitive inhibition by soluble antigen (17-1A) and was judged to be a non-specific phenomenon and not antibody. In contrast, post-immunization plasma immunoglobulin binding to 17-1A coated beads was readily inhibited by soluble antigen (17-1A). Thus, we believe that the double antigen assay system used in this study more clearly reflects immune response to 17-1A. Despite the administration of one or more large doses of 17-1A, human antibody response to this protein was prompt with antibody frequently detectable by Day 8 and appreciable levels of antibody achieved by Day 15 & 22. Further studies are underway to characterize this antibody response in regards to immunoglobulin subclass and anti-idiotype.

Biochemical and Epitope Analysis of 17-1A Antigen/ Production of Monoclonal Antibodies Against 17-1A.

Materials and Methods

Cells and Tissues

The human colon carcinoma cell lines DLD-1 and WiDr were obrtained form the American Type Culture Collection, Rockville, Md. The colon carcinoma line HT-29 was kindly provided by Dr. J. Fogh, Sloan Kettering Institute for Cancer Research, NY. Human tissues were snap-frozen in liquid nitrogen-cooled isopentane immediately after surgical removal.

Radiolabelling and Immunoprecipitation

Cells ($5 \times 10^7$) were surface-labelled by lactoperoxidase-mediated iodination using $^{125}$I as described. Pink, J. R. L. and Ziegler, A. (1979) in: *Research Methods in Immunology* Academic Press, N.Y. pp. 169–180. Immunosorbents prepared by binding MAbs to protein A-Sepharose (Sigma, St. Louis, Mo.) were added to labelled cell lysates at 4° C. for 2 hr. Bound material was eluted by boiling in sample buffer and analyzed by SDS-polyacrylamide gel electrophoresis (SDS-PAGE) according to Laemmli. Laemmli, U.K. (1970) *Nature*, 227: 680–685.

Selection of MAbs

Colon carcinoma tissue was obtained from a 51 year old female patient undergoing lobectomy of the liver because of a solitary metastasis. The 17-1A positive tumor tissue was carefully isolated, minced, homogenized and plasma membranes were purified as described by Touster et al. (1970) *J. Cell Biol.* 47 604–618. Fusion of the myeloma P3x63Ag8.653 and spleen cells from (C57BL/6 x Balb/c)F1 female mice was carried out using standard procedures (Galfre et al., (1977) *Nature* 266: 550–552) 3 days after a single i.p. injection of colon carcinoma plasma membrane preparations corresponding to 3 mg of protein together with Bordetella pertussis adjuvant. After fusion the cells were plated in HAT selective medium (hypoxanthine, aminopterin, thymidine) in 96-well microtiter plates containing mouse peritoneal macrophages. Supernatants of hybrids were screened by immunoperoxidase staining of frozen tissue sections derived from the liver metastasis taken for immunisation. Antibodies reacting with the colon carcinoma cells of the metastasis and the bile ducts in the adjacent liver, but not with hepatocytes, were further tested on a panel of non-malignant epithelial tissues listed in Table 5. Antibodies showing a 17-1A-like staining pattern in this context were cloned at least two times by limiting dilution.

TABLE 5

DISTRIBUTION OF 17-1A ANTIGEN IN NORMAL EPITHELIAL TISSUES[1]

| Tissue | Number tested/ Number positive | Remarks |
|---|---|---|
| Colon | 14/14 | strong staining of mucosa |
| Small intestine | 5/5 | strong staining of mucosa |
| Stomach | 6/9 | occasional weak staining of restricted areas |
| Gall bladder | 1/1 | strong staining of mucosa |
| Pancreas | 1/1 | strong staining of acini, ducts and islets of Langerhans |
| Mver | 6/6 | strong staining of bile ducts; hepatocytes negative |
| Kidney | 2/2 | Loops of Henle moderately, distal tubules strongly stained; proximal tubules, glomeruli negative |
| Lung | 2/2 | strong staining of bronchi; alveoli moderately stained |
| Thyroid gland | 3/3 | strong staining of follicular epithlium |
| Mammary gland | 3/3 | strong staining of lobules and ducts |
| Thymus | 0/1 | |
| Skin | 2/2 | strong staining or sweat glands; epidermis negative |

[1]as verified by immunohistochemical staining with MAbs 17-1A, M72, M74, M77 and M79, which showed a congruent staining pattern in all of the normal tissues examined.

Immunoblotting

Inmunoprecipitates were separated by SDS-PAGE, electrophoretically transferred to nitrocellulose membranes (Schleicher & Schull, Dassel, FRG) according to Towbin et al. (1979) *Proc. Natl. Acad. Sci.* USA 76: 4350–4354, and transferred antigen was visualized by an indirect immunoperoxidase technique, Holzmann, B. et al. (1985) *J. Exp. Med.* 161: 366–377.

Flow Cytometric Analysis

HT-29 cells were preincubated on ice with MAbs M72, M74, M77 or M79 as unconcentrated, 10x, or 50x concentrated supernatant, followed by incubation with biotinylated 17-1A antibody (10 ug/ml) and avidin-phycoerythrin (Becton-Dickinson, Mountain View, Calif.). The fluorescence profile was analyzed with an EPICS-V (Coulter Electronics, Hialeah, Fla.).

Immunohistochemistry

Frozen tissue sections were prepared and stained by an indirect immunoperoxidase technique essentially as described elsewhere. Gottlinger et al., (1985) *Int. J. Cancer* 35: 199–205. Briefly, air-dried sections (7 um) were fixed in acetone for 10 min., incubated with MAb (10 ug/ml or undiluted supernatant) for 30 min., washing in PBS and exposed for 30 min. to peroxidase-conjugated rabbit anti-mouse Ig antiserum (Dianova, Hamburg, FRG) diluted 1/200 in PBS containing 20% human serum. After washing in PBS the sections were incubated for 20 min. in 0.004% 3-amino-9-ethylcarbazole in 0.02 M barbital buffer, pH 7.4, containing 0.001% $H_2O_2$ and subsequently counterstained with Mayer's hemalum.

Results

Biochemical Analysis of the 17-1A Ag

Since the original biochemical analysis of the 17-1A Ag was only made for one human tumor cell line (HT-29), we investigated the nature of the 17-1A Ag expressed on two additional human colon carcinoma lines by surface iodination. Precipitation with MAb 17-1A revealed an identical single protein band in the three cell lines, DLD-1, WiDr and HT-29, which migrated with an apparent molecular weight of 37 kD in an SDS-PAGE system. As judged from fluorographic intensity, the amounts of antigen precipitable from the three cell lines were quite variable, with the colon carcinoma line DLD-1 providing the highest amount of radiolabelled antigen. Under reducing conditions, in which 2-mercaptoethanol was added to the precipitates prior to electrophoresis, a distinct band of 33 kD was obtained from all three cell lines. In addition, a major component of about 40 kD component was also found occasionally in HT-29 lysates. This band was apparently absent or could not be precipitated from WiDr cells.

Incubation of HT-29 cells with tunicamycin (2 ug/ml) for 24 hr resulted in the appearance of a new band of 30 kD under non-reducing and of 26 kD under reducing conditions, indicating that the 17-1A Ag contains 2 N-linked glycosylation sites. The glycoprotein nature of the 17-1A Ag was further substantiated by treatment of 17-1A precipitates with neuraminidase, which resulted in a slight but distinct reduction of the apparent molecular weight.

Epitope Analysis of the 17-1A Ag by new MAbs

Four new MAbs directed against the 17-1A Ag (M72, M74, M77, M79) were obtained by screening supernatants of hybridomas generated from mice immunized with membrane preparations from colon carcinoma metastases for a 17-1A-like reactivity on frozen tissue sections. All four antibodies precipitate proteins of identical molecular weight as seen with the original 17-1A antibody. In order to verify the identity of the antigens recognized by the new MAbs an extensive immunoblotting analysis was performed, whereby 17-1A immunoprecipitates were transferred to nitrocellulose paper after separation by SDS-PAGE and tested with the four new reagents. As shown previously, the four new antibodies bound to a 37 kD protein was not obtained with isotype-matched control MABs. To analyze the epitope specificity of the four new MAbs cross-blocking experiments were carried out. In a flow cytometry analysis the binding of a biotinylated 17-1A antibody to HT-29 cells was completely blocked by preincubation of the tumor cells with MAbs M72 and M74 (Table 6). In contrast, MAbs M77 and M79 showed no significant blocking activity for the biotinylated 17-1A antibody at all concentrations tested. We further analyzed whether the epitope specificity could be related to the idiotypes of the antibodies. All MAbs were analyzed for reactivity with an anti-idiotypic antiserum generated against the 17-1A antibody in goats (kindly provided by Dr. Dorothy Herlyn, The Wistar Institute, Philadelphia). The anti-idotypic antiserum strongly reacted with the two cross-blocking MAbs (M72 and M74), but was completely unreactive with the MAbs M77 and M79 (Table 6). These data suggest that mAbs 17-1A, M72 and M74 recognize the same or closely related epitopes on the 37 kD glycoprotein, while MAbs M77 and M79 define additional epitopes on this antigen.

TABLE 6

IDIOTYPE EXPRESSION AND CROSS-BLOCKING ACTIVITY OF DIFFERENT MABS DIRECTED AGAINST THE 17-1A ANTIGEN

|  | 17-1A | M72 | M74 | M77 | M79 |
| --- | --- | --- | --- | --- | --- |
| Reactivity with goat anti-Id 17-1A | +[a] | ++ | + | − | − |
| Cross-blocking activity | +[b] | ++ | ++ | − | − |

[a]in an ELISA, where the MAbs were coated to microtiter plates and subsequent binding of the goat anti-idiotypic antiserum to the MAbs was revealed by an indirect immunoperoxidase technique.
+optical density (OD) > 0.8;
++OD > 1.6;
−OD < 0.05
[b]Inhibition of binding or biotinylated 17-1A antibody tested in a flow cytometry analysis (see Materials and Methods):
+>25%,
++80%,
−<10%

Tissue Distribution of the 17-1A Ag

Using an indirect immunoperoxidase technique the 17-1A Ag was identified in various normal human organs and in a variety of human carcinomas. Concomitantly the four new MAbs were analyzed on parallel tissue sections. With respect to expression of the 17-1A Ag on colon tissue, it was found that normal mucosa was stained to a similar degree as colon carcinoma tissue in the fourteen patients examined. The 17-1A Ag was clearly detectable on the epithelial lining of the small intestine, the gall bladder, the bronchi and a variety of glandular structures, including the tyroid, the mammary gland, sweat glands and the exocrine as well as endocraine pancreas. Furthermore, the 17-1A Ag was found to be expressed in the kidney on distal tubules and the loops of Henle and in the liver by bile ducts, but not by hepatocytes.

In the stomach, normal mucosa usually showed a faint staining restricted to defined areas. However, in five patients with various degrees of intestinal metaplasia, present in an islet-like fashion in the gastric mucosa, those lesions were strongly stained by MAb 17-1A and the four new MAbs. The 17-1A Ag was also distinctly expressed in 9 of 9 gastric carcinomas tested.

Discussion

We have demonstrated that the 17-1A Ag is a glycoprotein migrating in SDS-PAGE with an apparent molecular weight of 37 kD under non-reducing conditions. Comparative analysis of three different colon carcinoma lines did not indicate a heteroegeneity of the 17-1A Ag when non-reducing conditions were applied. After reduction of the 17-1A precipitates with 2-mercaptoethanol and separation by SDS-PAGE a 33 kD band appeared which could be found with all the cell lines tested. In addition, a 40 kD band could be seen as a major component in the DLD-1 cell lysate and to a lesser degree in the lysate of HT-29 cells. This 40 kD band was virtually absent in lysates from WiDr cells. When precipitates from DLD-1 or HT-29 cells were processed in single experiments and analyzed in a parallel fashion under reducing and non-reducing conditions, again two bands of 33 and 40 kD appeared in the presence, but only a single band of 37 kD in the absence of 2-mercaptoethanol. Thus, reduction of the 17-1A Ag may result in the formation of two new forms of the molecule with different electrophoretic mobilities. Most probably the presence of intrachain disulfide bonds may account for this peculiar migration behavior. Alternatively, the 17-1A Ag may actually exist as a dimer of proteins exhibiting the same migration behavior under non-reducing conditions. The absence of the 40 kD molecule in WiDr lysates may then be explained by a differential accessability of this protein for lactoperoxidase-mediated iodination in different cell lines. Further analysis using metabolic labelling and cross-linking chemicals may be required to solve this question. Ross et al. have recently described a carcinoma-associated surface glycoprotein defined by their MAb GA733, that consists of 30 kD and 40 kD subunits. They suggest that the 17-1A antibody recognizes the same antigen, but binds to a different epitope than MAb GA733. Direct comparisons with the antibodies described here should reveal the relationship of these antigens.

The four new anti-17-1A Ag MAbs which we obtained displayed a tissue reactivity comparable to the original 17-1A antibody in normal organs and in tumors. So far no differential epitope expression was found in a variety of tissues examined. Two of these MAbs (M72 and M74) recognize a determinant closely related to that detected by MAb 17-1A as judged by cross-blocking experiments, whereas the MAbs M77 and M79 apparently define at least one additional epitope since they did not inhibit binding of the biotinylated 17-1A antibody. Interestingly, the epitope specificity of these MAbs was correlated with their reactivity with a goat anti-idiotypic antiserum. These MAbs will be of interest for analyzing their biological activities in conjunction with the original 17-1A antibody.

The 17-1A Ag is broadly expressed in non-malignant epithelial organs and is also present in most carcinomas originating from 17-1A-positive tissues. Quantitative differences in expression between normal and malignant tissue were not evident in a comparative immunohistochemical analysis of colorectal carcinomas and normal mucosa obtained from the same patients. However, a possible structural heterogeneity of this epithelial antigen on normal and malignant cells is not ruled out by the present analysis.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a gastrointestinal tumor comprising administering to a patient afflicted with a gastrointestinal tumor, a murine monoclonal antibody which specifically binds to an epitope of 17-1A antigen, said antibody being administered in multiple doses of about 400 milligrams or more per dose.

2. The method of claim 1 wherein the antibody is administered in multiple doses of about 400 to 1,000 milligrams for a total of about 1 to 5 grams of antibody.

3. The method of claim 1 wherein the gastrointestinal tumor is gastrointestinal adenocarcinoma, colorectal or pancreatic carcinoma.

4. The method of claim 3 wherein the multiple high dose therapy is administered as adjuvant therapy.

5. A method for treating a gastrointestinal tumor comprising administering to a patient afflicted with a gastrointestinal tumor, a murine monoclonal antibody which specifically binds to an epitope of 17-1A antigen, said antibody being administered in multiple doses of about 100 milligrams or more per dose for a total of about 0.1 to 5 grams of antibody, wherein the multiple doses are administered such that the patient sustains a high plasma level of antibody during the therapy.

6. The method of claim 5 wherein the multiple doses are administered at an interval between about one day to about one week.

7. The method of claim 6 wherein the gastrointestinal tumor is gastrointestinal adenocarcinoma, colorectal or pancreatic carcinoma.

8. A method for treating a gastrointestinal tumor comprising administering to a patient afflicted with a gastrointestinal tumor, a murine monoclonal antibody which specifically binds to an epitope of 17-1A antigen, said antibody being administered as adjuvant therapy in multiple doses of 100 milligrams or more per dose for a total of about 0.1 to 5 grams of antibody.

9. The method of claim 8 wherein th gastrointestinal tumor is gastrointestinal adenocarcinoma, colorectal or pancreatic carcinoma.

10. A method of claim 8 wherein the first dose of said antibody is of about 400 milligrams or more per dose.

11. A method of claim 8 wherein said antibody is administered as adjuvant therapy to surgery.

12. A method for treating a gastrointestinal tumor comprising administering to a patient afflicted with a gastrointestinal tumor, a murine monoclonal antibody which specifically binds to an epitope of 17-1A antigen, said antibody being administered in multiple doses, wherein the first dose is of about 400 milligrams or more per dose and the second or subsequent dose is of about 100 milligrams or more per dose, for a total of about 0.1 to 5 grams of antibody.

13. A method for treating a carcinoma originating from a 17-1A-positive tissue comprising administering to a patient afflicted with a carcinoma originating from a 17-1A-positive tissue, a monoclonal antibody which specifically binds to an epitope of 17-1A antigen, said antibody being administered in multiple doses of about 100 milligrams or more per dose, wherein the multiple doses are administered such that the patient sustains a high plasma level of antibody during therapy.

14. A method for treating a carcinoma originating from a 17-1A-positive tissue comprising administering to a patient afflicted with a carcinoma originating from a 17-1A-positive tissue, a monoclonal antibody which specifically binds to an epitope of 17-1A antigen, said antibody being administered in multiple doses, wherein the first dose is of about 400 milligrams or more per dose and the second or subsequent dose is of about 100 milligrams or more per dose.

15. A method for treating a carcinoma originating from a 17-1A-positive tissue comprising administering to a patient afflicted with a carcinoma originating from a 17-1A-positive tissue, a monoclonal antibody which specifically binds to an epitope of 17-1A antigen, said antibody being administered as adjuvant therapy in multiple doses of about 100 milligrams or more per dose.

16. A method for treating a carcinoma originating from bronchial tissue or tissue of glandular structure comprising administering to a patient afflicted with a carcinoma originating from bronchial tissue or tissue of glandular structure, a monoclonal antibody which specifically binds an epitope of 17-1A antigen, said antibody being administered in multiple doses for a total dose of about 0.1 to 5 grams.

17. A method of claim 16 wherein said antibody is administered as adjuvant therapy to surgery.

\* \* \* \* \*